US010166538B2

(12) United States Patent
Syvret et al.

(10) Patent No.: US 10,166,538 B2
(45) Date of Patent: Jan. 1, 2019

(54) ACTIVATION AND REGENERATION OF FLUORINATION CATALYSTS, AND FLUORINATION PROCESS

(71) Applicant: Arkema Inc., King of Prussia, PA (US)

(72) Inventors: Robert G. Syvret, Allentown, PA (US); Patrick K. Janney, Ridley Park, PA (US); Sri R. Seshadri, Holland, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/763,874

(22) PCT Filed: Jan. 20, 2014

(86) PCT No.: PCT/US2014/012166
§ 371 (c)(1),
(2) Date: Jul. 28, 2015

(87) PCT Pub. No.: WO2014/120493
PCT Pub. Date: Aug. 7, 2014

(65) Prior Publication Data
US 2015/0360218 A1  Dec. 17, 2015

Related U.S. Application Data

(60) Provisional application No. 61/757,768, filed on Jan. 29, 2013.

(51) Int. Cl.
| | | |
|---|---|---|
| *C07C 17/20* | (2006.01) | |
| *B01J 23/26* | (2006.01) | |
| *B01J 23/90* | (2006.01) | |
| *B01J 23/92* | (2006.01) | |
| *B01J 38/46* | (2006.01) | |
| *B01J 27/32* | (2006.01) | |
| *B01J 37/26* | (2006.01) | |
| *B01J 23/86* | (2006.01) | |
| *C07C 17/21* | (2006.01) | |
| *B01J 27/138* | (2006.01) | |
| *B01J 23/34* | (2006.01) | |
| *B01J 27/132* | (2006.01) | |

(52) U.S. Cl.
CPC ............... *B01J 38/46* (2013.01); *B01J 23/26* (2013.01); *B01J 23/86* (2013.01); *B01J 23/92* (2013.01); *B01J 27/138* (2013.01); *B01J 27/32* (2013.01); *B01J 37/26* (2013.01); *C07C 17/202* (2013.01); *C07C 17/206* (2013.01); *C07C 17/21* (2013.01); *B01J 23/34* (2013.01); *B01J 23/90* (2013.01); *B01J 27/132* (2013.01); *Y02P 20/584* (2015.11)

(58) Field of Classification Search
CPC ..... C07C 17/201; C07C 17/21; C07C 17/206; C07C 17/202; B01J 38/46; B01J 27/138; B01J 27/32; B01J 27/132; B01J 37/26; B01J 23/86; B01J 23/26; B01J 23/34; B01J 23/90; Y02P 20/584
See application file for complete search history.

(56) References Cited

U.S. PATENT DOCUMENTS

| | | | | |
|---|---|---|---|---|
| 4,145,311 | A * | 3/1979 | von Halasz | ............... B01J 27/32 502/36 |
| 5,227,350 | A | 7/1993 | Scott et al. | |
| 5,880,049 | A | 3/1999 | Lacroix et al. | |
| 6,524,990 | B2 * | 2/2003 | Syvret | ...................... B01J 27/12 502/224 |
| 6,639,115 | B2 * | 10/2003 | Requieme | ............. C07C 17/206 570/165 |
| 7,074,973 | B2 * | 7/2006 | Nappa | .................... B01J 23/864 570/165 |
| 2010/0210882 | A1 | 8/2010 | Sharratt et al. | |
| 2010/0210883 | A1 | 8/2010 | Mukhopadhyay et al. | |
| 2011/0114075 | A1 * | 5/2011 | Mills | ........................ C01B 3/00 126/263.01 |
| 2014/0135538 | A1 | 5/2014 | Cho et al. | |
| 2015/0110685 | A1 | 4/2015 | Cho et al. | |

FOREIGN PATENT DOCUMENTS

| | | | | |
|---|---|---|---|---|
| EP | 0439338 | A1 * | 7/1991 | ............. B01J 31/02 |
| WO | WO 2012/098422 | A1 | 7/2012 | |

OTHER PUBLICATIONS

Belter, Randolph K., et al; "Nitrogen Trifluoride as an Oxidative Co-Reagent in High Temperature Vapor Phase Hydrofluorinations"— Journal of Fluorine Chemistry 127 (2006) pp. 816-820.

* cited by examiner

*Primary Examiner* — Medhanit W Bahta
(74) *Attorney, Agent, or Firm* — Steven D. Boyd

(57) ABSTRACT

A fluorination catalyst such as a chromium oxide-based fluorination catalyst may be activated or reactivated by contacting the catalyst. with a source of reactive fluorine, for example nitrogen trifluoride (NF3) or fluorine (F2). Fluorinated compounds may be prepared by the gas phase reaction of hydrogen fluoride (HF) with various substrates such as chlorinated compounds. A number of metal oxide-based catalysts have been developed for this purpose.

10 Claims, No Drawings

US 10,166,538 B2

ACTIVATION AND REGENERATION OF FLUORINATION CATALYSTS, AND FLUORINATION PROCESS

This present application is the national phase under 35 USC § 371 of prior PCT International Application Number PCT/US2014/012166 filed Jan. 20, 2014 which designated the United States of America and claimed priority to U.S. Provisional Patent Application Ser. No. 61/757,768 filed Jan. 29, 2013.

FIELD OF THE INVENTION

The invention relates to methods for activating and regenerating catalysts used to fluorinate substrates such as chlorinated compounds using hydrogen fluoride.

BACKGROUND OF THE INVENTION

Fluorinated compounds may be prepared by the gas phase reaction of hydrogen fluoride (HF) with various substrates such as chlorinated compounds. A number of metal oxide-based catalysts have been developed for this purpose. However, such catalysts typically lose activity with prolonged use. Additionally, inactive catalyst precursors often must be activated in order to prepare such fluorination catalysts.

Various methods for activating and reactivating metal oxide-based fluorination catalysts, as well as methods for extending the useful life of such catalysts, have been investigated. However, these methods are known to possess certain disadvantages. For example, oxygen ($O_2$) may be co-fed continuously or intermittently during the fluorination reaction or during reactivation for the purpose of oxidizing and removing carbonaceous deposits, which tend to inhibit catalyst activity, from the catalyst surface. However, water and carbon dioxide typically are produced as by-products. The water generated may itself damage and deactivate the catalyst due to phase changes triggered by the repeated addition and loss of water from the catalyst. The presence of water in the reactor system may also lead to corrosion or erosion of fluorination equipment.

Accordingly, the development of improved, effective procedures for both activating and reactivating catalysts for use in fluorination reactions which avoid the generation of water would be of interest.

SUMMARY OF THE INVENTION

One aspect of the invention provides a method of reactivating a spent or depleted fluorination catalyst (in particular, a metal oxide-based fluorination catalyst such as a chromium oxide-based fluorination catalyst), comprising contacting the spent or depleted fluorination catalyst with an agent that is a source of reactive fluorine such as $NF_3$ or $F_2$. The fluorination catalyst may have been used to catalyze the fluorination of a chlorinated compound such as a chloroolefin or chloroalkane using HF. The contacting may be carried out in a gas (vapor) phase at a temperature of about 100° C. to about 400° C., for example.

Another aspect of the invention furnishes a fluorination process, alternately comprising reaction stages and regeneration stages, wherein the reaction stages comprise reacting a compound with HF in a gas phase in the presence of a fluorination catalyst to produce a fluorinated compound and the regeneration stages comprise contacting the fluorination catalyst with an agent that is a source of reactive fluorine such as $NF_3$ or $F_2$. Such a process may additionally comprise a preliminary activation stage which comprises contacting a fluorination catalyst precursor with an agent that is a source of reactive fluorine such as $NF_3$ or $F_2$.

A method of activating a fluorination catalyst is additionally supplied by the invention, comprising contacting a fluorination catalyst precursor with an agent that is a source of reactive fluorine such as $NF_3$ or $F_2$. The contacting may, for example, be carried in a gas phase at a temperature of about 100° C. to about 400° C.

The activation and reactivation processes of the present invention may be carried out in situ (i.e., the catalyst may be activated or reactivated while in place in the equipment used for fluorination of a substrate) or ex situ (i.e., the catalyst may be activated or reactivated in accordance with the invention in equipment other than the fluorination equipment and subsequently transferred to the fluorination equipment).

DETAILED DESCRIPTION OF THE INVENTION

Activation/Reactivation Agents

The present invention utilizes a source of reactive fluorine such as nitrogen trifluoride ($NF_3$) or fluorine ($F_2$) or mixtures thereof as an agent for activating and/or reactivating fluorination catalysts. Such agents are fluorine-containing substances other than HF which are capable of supplying fluorine in a form which reacts with the catalyst so as to increase or restore its catalytic activity. Other useful agents for such purposes may include, for example, interhalogens (e.g., $ClF$, $ClF_3$, $ClF_5$, $BrF_3$, $BrF_5$, $IF_5$, and $IF_7$); hypofluorites (e.g., $CF_3OF$); fluorinated peroxides such as $CF_3OOCF_3$, as well as other fluoride and oxide fluoride compounds such as $OF_2$, $O_2F_2$, $N_2F_2$, $N_2F_4$, $SF_4$, $SOF_4$, $SOF_2$, $XeF_2$, $XeF_4$, $XeF_6$, $KrF_2$, $FNO$, $FNO_2$, and $FClO_3$.

The catalyst activation/reactivation agent may be admixed with one or more other substances as it is contacted with the catalyst precursor or deactivated catalyst. For example, the agent(s) which serve as a source of reactive fluorine may be present in combination with one or more of HF, HCl, chlorocarbons, fluorocarbons, $O_2$, $N_2$, CO, $CO_2$ and the like. Particular examples of such admixtures include, but are not limited to: $HF+NF_3$; $HF+HCl+NF_3$; $HF+$chlorocarbons$+NF_3$; and $O_2+NF_3$. Such admixtures may be obtained as a result of recycling the stream containing the activation/reactivation agent after the agent is passed over or through the catalyst.

Fluorination Reaction

In the fluorination reaction of the invention, a substrate such as a chlorinated compound is converted to a fluorinated compound through a reaction with hydrogen fluoride (HF) in the presence of a metal oxide-based catalyst. Where the substrate is a halogenated compound such as a chlorinated compound, the substrate may undergo a halogen exchange reaction catalyzed by the metal oxide-based catalyst (e.g., F is substituted for Cl). The "chlorinated compound" can be any molecule having at least one chlorine atom, and the "fluorinated compound" can be any molecule having at least one fluorine atom. The fluorination reaction may involve a reaction other than a halogen exchange reaction. For example, a fluorine atom may be substituted (exchanged) for a hydrogen atom on the substrate.

In one embodiment of the invention, the chlorinated compound is a C1 to C8 alkane or alkene compound, which may be linear or branched, having one or more substituents selected from F, Cl, I and Br, with at least one of the substituents being Cl. Mixtures of such chlorinated compounds may also be used. The fluorinated compound may be a C1 to C8 alkane or alkene compound, which may be linear or branched, having one or more substituents selected from F, Cl, I and Br, at least one of the substituents being F. Mixtures of such fluorinated compounds may be produced.

In one particular embodiment, the chlorinated compound is a C3 alkane or alkene compound having one or more substituents selected from F, Cl, I and Br, at least one of the substituents being Cl; and the fluorinated compound is a C3 alkene compound having one or more substituents selected from F, Cl, I and Br, at least one of the substituents being F. Alternatively, the chlorinated compound can be a C4 alkane or alkene compound having one or more substituents selected from F, Cl, I and Br, at least one of the substituents being Cl; and the fluorinated compound is a C4 alkene compound having one or more substituents selected from F, Cl, I and Br, at least one of the substituents being F. According to one embodiment, the fluorinated compound is a hydrofluoroolefin (and thus has no chlorine substituent). Typically, during the reaction at least one Cl substituent in the chlorinated compound is replaced by an F substituent.

The conversion of the chlorinated compound to the fluorinated compound may comprise direct conversion (i.e. in a single reaction step or under essentially one set of reaction conditions) or indirect conversion (i.e., through two or more reaction steps or using more than one single set of reaction conditions).

Illustrative fluorination reactions in accordance with the invention include the following:

2-chloro-3,3,3-trifluoro-1-propene (HFCO-1233xf) to 2,3,3,3-tetrafluoro-1-propene (HFO-1234yf);

1,1,1,2,3-pentachloropropane (HCC-240db) to 2,3,3,3-tetrafluoro-1-propene (HFO-1234yf);

1,1,2,2,3-pentachloropropane (HCC-240aa) to 2,3,3,3-tetrafluoro-1-propene (HFO-1234yf);

2,3-dichloro-1,1,1-trifluoropropane (HCFC-243db) to 2,3,3,3-tetrafluoro-1-propene (HFO-1234yf);

1,1,2,3 tetrachloro-1-propene (HCO-1230xa) to 2,3,3,3-tetrafluoro-1-propene (HFO-1234yf);

2,3,3,3 tetrachloro-1-propene (HCO-1230xf) to 2,3,3,3-tetrafluoro-1-propene (HFO-1234yf);

1,1,1,2,3-pentachloropropane (HCC-240db) to 2-chloro-3,3,3-trifluoro-1-propene (HFCO-1233xf);

1,1,2,2,3-pentachloropropane (HCC-240aa) to 2-chloro-3,3,3-trifluoro-1-propene (HFCO-1233xf);

2,3-dichloro-1,1,1-trifluoropropane (HCFC-243db) to 2-chloro-3,3,3-trifluoro-1-propene (HFCO-1233xf);

1,1,2,3 tetrachloro-1-propene (HCO-1230xa) to 2-chloro-3,3,3-trifluoro-1-propene (HFCO-1233xf);

2,3,3,3 tetrachloro-1-propene (HCO-1230xf) to 2-chloro-3,3,3-trifluoro-1-propene (HFCO-1233xf).

The fluorination reaction can be carried out with an HF molar ratio of HF to compound to be fluorinated typically from 3:1 to 150:1, at a contact time from 6 to 100 s and a pressure from atmospheric pressure to 20 bars. The catalyst bed temperature can be, for example, from 100 to 450° C.

Catalyst

The fluorination catalyst used in the present invention can be supported or unsupported. It can be, for example, a catalyst based on a metal including a transition metal oxide or a derivative thereof. In one embodiment, the catalyst is a chromium oxide-based catalyst. Suitable catalysts include, but are not limited to, metal oxide-based bulk and supported catalysts, including doped and undoped catalysts. A catalyst precursor to be activated in accordance with one aspect of the invention may be any metal oxide (e.g., corresponding to the general empirical formula $M_xO_y$, wherein x is 1-2 and y is selected such that the valency of M is satisfied). The metal M may be, for example, a first or second row transition metal. Once activated, the catalyst may be a metal oxide fluoride corresponding to the general empirical formula $M_xO_yF_z$, wherein x is 1-2 and y and z are selected such that the valency of M is satisfied. When M is chromium (Cr), the valency of M is typically 3-6.

The metal in the catalyst is converted to metal derivatives during activation (or regeneration), including oxides, halides or oxide halides. The metals in the catalyst are typically present in the form of metal oxides, oxychlorides, chlorides, chlorofluorides, oxychlorofluorides, oxyfluorides or fluorides. Thus, when the fluorination catalyst is a chromium oxide-based catalyst, the catalyst typically contains an oxide, oxide halide (for example, an oxyfluoride) and/or halide of chromium (for example, a fluoride of chromium).

A particularly suitable catalyst for use in the present invention is a high surface area unsupported chromium oxide-based catalyst. However, supported chromium oxide-based catalysts are also suitable for use.

The catalyst can optionally contain a low level of one or more co-catalysts (sometimes referred to as dopants) such as Co, Zn, Mn, Mg, V, Mo, Te, Nb, Sb, Ta, P, Ni, Ca, Sr, Ba, Na, K, Rb, Cs, Cd, Hg, Cu, Ag, Au, Pd, Pt, W, Ti, Zr, and/or Hf.

In one embodiment of the invention, the fluorination catalyst is an unsupported chromium catalyst which can optionally contain low levels of one or more co-catalysts selected from cobalt, nickel, zinc or manganese, prepared by processes known in the art, such as impregnation, mixed powder, co-precipitation and the like.

The amount of co-catalyst, when present, can be varied between 1 to 10 wt %, e.g., between 1 to 5 wt %. The co-catalyst can be added to the catalyst by processes known in the art such as adsorption from an aqueous or organic solution, followed by solvent evaporation.

The catalyst precursor, before activation, may be subjected to a drying step, such as a step which comprises passing a drying gas, such as nitrogen, over the catalyst precursor. The drying step can be carried out at a pressure of from atmospheric pressure up to 20 bars, for example. The temperature of the catalyst precursor during the drying step can range from room temperature up to 400° C., e.g., from about 175° C. to about 275° C. with a volumetric flow rate of the activating agent corresponding to a contact time in the catalyst bed of from about 1 to 100 s, e.g., from about 10 to 40 s, for an activation duration of from about 0.5 to 50 hours, e.g., between 1 to 5 hours. After the drying step, the catalyst precursor needs to be activated (i.e., converted to a substance having high catalytic activity for the fluorination of a substrate such as a chlorinated compound using HF).

Activation of the Catalyst

The present inventors have found that the activation of the above catalysts using an agent that is a source of reactive fluorine such as $NF_3$ and/or $F_2$ makes it possible to significantly improve the efficiency of the fluorination process. The activation process may comprise activating the catalyst precursor using at least one activating agent. The temperature of this activation step can range from about 100 to about 500° C., e.g., from about 300 to about 400° C., with a volumetric flow rate of the activating agent corresponding to a contact time in the catalyst bed of from about 1 to about 200 s, for an activation duration of from about 10 to about 300 hours.

The above activation processes can be carried out at a pressure of from atmospheric pressure up to about 20 bars. The activating agent can be fed to the system with an inert gas such as nitrogen. The proportion of activating agent can range from about 1 to 100 mole % of the mixture. In one embodiment, $NF_3$ is employed as the activating agent and is contacted with the catalyst precursor in pure or essentially pure form (i.e., $NF_3$ comprises from 90 to 100 mole % of the gas contacted with the catalyst precursor).

Regeneration (Reactivation) of the Catalyst

The present inventors have also found that the efficiency of the fluorination reaction tends to decrease over time, but that it can be increased again up to, and even above, the initial efficiency, by subjecting the catalyst to regeneration stages wherein it is contacted with an agent that is a source of reactive fluorine such as $NF_3$ or $F_2$, in a similar way as during the initial activation stage. The temperature during the regeneration step can range from about 100 to about 500° C., with a contact time of from about 1 to about 200 s, for about 1 to about 200 hours. The regeneration step can be carried out at a pressure from atmospheric pressure to about 20 bars. The reactivating agent can be fed to the system with an inert gas such as nitrogen. The proportion of reactivating agent can range from about 1 to about 100 mole % of the mixture. In one embodiment, $NF_3$ is employed as the reactivating agent and is contacted with the spent catalyst in pure or essentially pure form (i.e., $NF_3$ comprises from 90 to 100 mole % of the gas contacted with the spent catalyst).

When reaction stages alternate with regeneration stages, the duration of each reaction stage can be from 50 to 2000 hours, e.g., from 200 to 1000 hours, and the duration of each regeneration stage can be from 1 to 200 hours, e.g., from 2 to 20 hours.

EXAMPLES

Example 1: Activation with Pure $NF_3$

Pellets of chromium oxide ($Cr_2O_3$) doped with Zn were crushed and sieved to uniform particle size of 8 to 20 mesh. A 1" o.d. tubular reactor was loaded with a bed containing 46 cc (40.65 g=268 mmol) of the sized catalyst precursor. The bed was heated to 225° C. and flushed with dry $N_2$ for 2.5 hours to facilitate removal of volatiles. The bed was then heated to 350° C. and pure $NF_3$ was flowed through the bed at approximately 5 sccm for 24 hours. After the specified time, $NF_3$ flow was terminated and replaced by 100 sccm dry $N_2$. Nitrogen was flowed for approximately 72 hours. After the specified time, $N_2$ was replaced by a reactant mixture consisting of HF, air, and 3,3,3-trifluoro-2-chloropropene, ($CF_3C(Cl)=CH_2$, hereafter called 1233xf), flowing at ambient pressure with a contact time of 20 seconds through the catalyst bed heated to 350° C. The mixture contained reactants in the molar ratio HF:1233xf:$O_2$=20:1:0.2.

The product exiting the reactor was passed through a caustic scrubber and analyzed subsequently online by gas chromatography (GC). Initial conversion of 1233xf was approximately 56% with steady-state selectivity of 73% 2,3,3,3-tetrafluoropropene (hereafter called 1234yf) and 23% 1,1,1,3,3-pentafluoropropane (hereafter called 245cb). The reactant mixture was flowed continuously for approximately 100 hours after which the reactant mixture was replaced by $N_2$ for a period of 10 days. Following the 10 day purge with $N_2$, the reactant mixture was resumed as before and continued for an additional 250 hours. During these 250 hours the conversion declined slowly from approximately 50% to a steady-state value of 23%. Selectivity remained at 73% 1234yf and 23% 245cb. After this 250 hour reaction period the catalyst was deemed "deactivated" as it was at its lowest 1233xf conversion rate. The catalyst bed was held at 350° C. and purged with $N_2$ for 4 days before being used in Example 2.

Example 2: Reactivation of Deactivated Catalyst with Pure $NF_3$

The deactivated catalyst remaining at the end of Example 1 was reactivated with pure $NF_3$ as follows. Pure $NF_3$ was flowed at approximately 5 sccm through the depleted bed for 22 hours at 350° C. During the reactivation with $NF_3$ an exotherm was observed in the bed during the initial few hours. In addition, volatile products of the reactivation process were observed by online GC analysis only during the first 293 minutes of activation, after which just $NF_3$ was observed flowing from the bed.

Following the 22 hour reactivation period, the pure $NF_3$ flow was replaced by a reactant mixture similar to that described in Example 1 (HF:1233xf:$O_2$=20:1:0.2), flowing at ambient pressure with a contact time of 20 seconds through the catalyst bed heated to 350° C.

The product exiting the reactor was passed through a caustic scrubber and analyzed online by gas chromatography (GC). Initial conversion of 1233xf was approximately 60% with steady-state selectivity of 70% 1234yf and 28% 245cb. The reactant mixture was flowed continuously for approximately 100 hours after which the reactant mixture was replaced by $N_2$ for a period of 3 days.

Example 3: Activation Using $NF_3$ Followed by Air

Pellets of chromium oxide ($Cr_2O_3$) doped with Zn were crushed and sieved to uniform particle size of 8 to 20 mesh. A 1" o.d. tubular reactor was loaded with a bed containing 100 cc (94.9 g=624 mmol) of the sized catalyst precursor. The bed was heated to 275° C. and flushed with pure $N_2$ for 72 hours to facilitate removal of volatiles. The flow of pure $N_2$ was replaced with a mixture containing 5 sccm pure $NF_3$ and 100 sccm pure $N_2$ and this flow was continued for approximately 24 hours. The bed temperature was then raised to 350° C. and pure $NF_3$ was added at 5 sccm until approximately 642 mmol total $NF_3$ had been added. Following the addition of $NF_3$, air was added at 25 sccm for a period of 4 days at 350° C. and at ambient pressure. After the specified time the flow of air was replaced by a reactant mixture similar to that described in Example 1 with the exception that 4% $O_2$ was used (HF:1233xf:$O_2$=20:1:0.04). The reactant mixture was flowed continuously at 1 bar absolute pressure with a contact time of 20 seconds through the catalyst bed heated to 350° C.

The product exiting the reactor was passed through a caustic scrubber and analyzed subsequently online by gas chromatography (GC). Initial conversion of 1233xf was approximately 58% with steady-state selectivity during the first 90 hours of reaction of 73% 1234yf and 25% 245cb. The reactant mixture was flowed continuously for approximately 90 hours after which the reactant mixture was replaced by air for a period of 10 days. Following the 10 day reactivation with air, the reactant mixture was resumed as before and continued for an additional 260 hours. During the 260 hour reaction period the conversion declined slowly from approximately 65% to about 30% while the selectivities varied from 33% to 50% for 1234yf and from 62% to 47% for 245cb. Following the 260 hour reaction period the reactant mixture was replaced by air for a 3 day reactivation. Following reactivation, feeding of the reactant mixture was resumed as before and continued for an additional 400 hours. During the 400 hour reaction period the conversion declined slowly from approximately 65% to about 35% while the selectivities varied from 35% to 40% for 1234yf and from 62% to 57% for 245cb. Following the 400 hour reaction period the experiment was terminated.

Example 4: Attempted Activation Using Air and $NF_3$

Pellets of chromium oxide ($Cr_2O_3$) doped with Zn were crushed and sieved to uniform particle size of 8 to 20 mesh. A 1" o.d. tubular reactor was loaded with a bed containing 23 cc (20.74 g=140 mmol) of the sized catalyst precursor. The bed was heated to 325° C. and flushed with pure air for 3 hours to facilitate removal of volatiles. The flow of pure air was replaced with a mixture containing 5 sccm pure $NF_3$ and 75 sccm pure air; however, an exotherm was observed so the flows were reduced to 0.5 sccm pure $NF_3$ and 7.5 sccm pure air. The bed pressure was increased from ambient to approximately 37 psig. The mixture of $NF_3$ and air was continued until approximately 500 mmol $NF_3$ had been added. After the specified time, the flow of $NF_3$ and air was replaced by a reactant mixture similar to that described in Example 1 (HF:1233xf:$O_2$=20:1:0.2)), flowing at 3.5 bar absolute pressure with a contact time of 20 seconds through the catalyst bed heated to 350° C.

The product exiting the reactor was passed through a caustic scrubber and analyzed subsequently online by gas chromatography (GC); however, it was determined that little if any 1233xf was converted to products. At this point, the reactant mixture was replaced for a short period by $NF_3$ followed by air followed by a flow of air that was continued for 4 days. After the specified time, the air was replaced with the reactant mixture; however, the 1233xf conversion was <10% and as such, the catalyst was deemed "not activated."

Example 5: Activation Under Pressure Using $NF_3$ Followed by Air

Pellets of chromium oxide ($Cr_2O_3$) doped with Zn were crushed and sieved to uniform particle size of 8 to 20 mesh. A 1" o.d. tubular reactor was loaded with a bed containing 46 cc (40.11 g=264 mmol) of the sized catalyst precursor. The bed was heated to 200° C. and flushed with pure $N_2$ to facilitate removal of volatiles. The flow of $N_2$ was replaced with a mixture at ambient pressure containing, initially, 5 sccm pure $NF_3$ and 20 sccm $N_2$ which was replaced ultimately with pure $NF_3$ flowing at 5 sccm and at 3.5 bar absolute pressure for the duration of the $NF_3$ addition. In total, about 10 mol % excess $NF_3$ was used. After the addition of $NF_3$ was terminated, pure air was flowed at 350° C. and 3.5 bar absolute pressure for a period of 6 days. After the specified time the flow of air was replaced by a reactant mixture similar to that described in Example 1 (HF:1233xf:$O_2$=20:1:0.2)), flowing at 3.5 bar absolute pressure with a contact time of 20 seconds through the catalyst bed heated to 350° C.

The product exiting the reactor was passed through a caustic scrubber and analyzed subsequently online by gas chromatography (GC). Initial conversion of 1233xf was approximately 36% but declined steadily over the course of the first 70 hours to a final value <10%. The steady-state selectivities reached during the first 70 hours of reaction were 65% 1234yf and 25% 245cb. The reactant mixture was flowed continuously for approximately 70 hours after which the reactant mixture was replaced by air for a period of 3 days. Following the 3 day reactivation attempt with air, feeding of the reactant mixture was resumed as before; however, the conversion declined rapidly from about 30% to about 10% over a period of about 50 hours and thus the catalyst was deemed not adequately activated and the experiment was terminated.

What is claimed is:

1. A method of reactivating a spent or depleted chromium oxide-based fluorination catalyst, comprising contacting the spent or depleted chromium oxide-based fluorination catalyst with an agent that is a source of reactive fluorine selected from the group consisting of interhalogens, hypofluorites, fluorinated peroxides, $OF_2$, $O_2F_2$, $N_2F_2$, $N_2F_4$, $SOF_4$, $SOF_2$, $XeF_2$, $XeF_4$, $XeF_6$, $KrF_2$, FNO, $FNO_2$, $FClO_3$, and mixtures thereof.

2. The method of claim 1, wherein the chromium oxide-based fluorination catalyst is a bulk (unsupported) or supported chromium oxide-based fluorination catalyst.

3. The method of claim 1, wherein the fluorination catalyst has been used to catalyze the fluorination of a chloroolefin or chloroalkane using HF.

4. The method of claim 1, wherein the contacting is carried in a gas phase at a temperature of about 330° C. to about 400° C.

5. A method of activating a chromium oxide-based fluorination catalyst, comprising contacting a chromium oxide-based fluorination catalyst precursor with an agent that is a source of reactive fluorine selected from the group consisting of interhalogens, hypofluorites, fluorinated peroxides, $OF_2$, $O_2F_2$, $N_2F_2$, $N_2F_4$, $SOF_4$, $SOF_2$, $XeF_2$, $XeF_4$, $XeF_6$, $KrF_2$, FNO, $FNO_2$, $FClO_3$, and mixtures thereof.

6. The method of claim 5, wherein the chromium oxide-based fluorination catalyst precursor is comprised of bulk (unsupported) or supported chromium oxide.

7. The method of claim 5, wherein the contacting is carried in a gas phase at a temperature of about 300° C. to about 400° C.

8. A fluorination process, alternately comprising reaction stages and regeneration stages, wherein the reaction stages comprise reacting a compound with HF in gas phase in the presence of a chromium oxide-based fluorination catalyst to produce a fluorinated compound and the regeneration stages comprise contacting the fluorination catalyst with an agent that is a source of reactive fluorine selected from the group consisting of interhalogens, hypofluorites, fluorinated peroxides, $OF_2$, $O_2F_2$, $N_2F_2$, $N_2F_4$, $SF_4$, $SOF_4$, $SOF_2$, $XeF_2$, $XeF_4$, $XeF_6$, $KrF_2$, FNO, $FNO_2$, $FClO_3$, and mixtures thereof.

9. The fluorination process of claim 8, wherein the chromium oxide-based fluorination catalyst is a bulk (unsupported) or supported chromium oxide-based fluorination catalyst.

10. The fluorination process of claim 8, additionally comprising a preliminary activation stage which comprises contacting a fluorination catalyst precursor with an agent that is a source of reactive fluorine.

* * * * *